(12) United States Patent
Yodfat et al.

(10) Patent No.: US 8,632,497 B2
(45) Date of Patent: Jan. 21, 2014

(54) SKIN SECURABLE DRUG DELIVERY DEVICE WITH A SHOCK ABSORBING PROTECTIVE SHIELD

(75) Inventors: Ofer Yodfat, Modi'in (IL); Illai Gescheit, Tel Aviv (IL)

(73) Assignee: Roche Diagnostics Operations Inc., Indianapolis, IN (US)

( * ) Notice: Subject to any disclaimer, the term of this patent is extended or adjusted under 35 U.S.C. 154(b) by 0 days.

(21) Appl. No.: 13/122,204

(22) PCT Filed: Oct. 11, 2009

(86) PCT No.: PCT/IL2009/000973
§ 371 (c)(1),
(2), (4) Date: Apr. 1, 2011

(87) PCT Pub. No.: WO2010/041261
PCT Pub. Date: Apr. 15, 2010

(65) Prior Publication Data
US 2011/0202005 A1    Aug. 18, 2011

Related U.S. Application Data

(60) Provisional application No. 61/104,138, filed on Oct. 9, 2008.

(51) Int. Cl.
*A61M 5/142* (2006.01)
(52) U.S. Cl.
USPC .......................................... 604/151; 604/131
(58) Field of Classification Search
USPC ............ 604/890.1, 65, 93.01, 131, 140–143, 604/151
See application file for complete search history.

(56) References Cited

U.S. PATENT DOCUMENTS

| | | | |
|---|---|---|---|
| 5,370,622 A * | 12/1994 | Livingston et al. | 604/151 |
| 6,261,259 B1 * | 7/2001 | Bell | 604/93.01 |
| 6,589,229 B1 * | 7/2003 | Connelly et al. | 604/890.1 |
| 7,014,625 B2 * | 3/2006 | Bengtsson | 604/131 |
| 7,611,481 B2 * | 11/2009 | Cleary et al. | 604/46 |
| 2004/0004680 A1 | 1/2004 | Kim | |
| 2004/0064096 A1 * | 4/2004 | Flaherty et al. | 604/131 |
| 2004/0133166 A1 | 7/2004 | Moberg | |
| 2007/0106218 A1 | 5/2007 | Yodfat et al. | |
| 2007/0191702 A1 | 8/2007 | Yodfat et al. | |
| 2008/0214916 A1 | 9/2008 | Yodfat et al. | |
| 2008/0215035 A1 * | 9/2008 | Yodfat et al. | 604/513 |

FOREIGN PATENT DOCUMENTS

| | | |
|---|---|---|
| WO | WO 99/65547 | 12/1999 |
| WO | WO 01/58506 | 8/2001 |
| WO | WO 03/099351 | 12/2003 |
| WO | WO 2006/089958 | 8/2006 |

(Continued)

OTHER PUBLICATIONS

International Search Report for PCT Application No. PCT/IL2009/000973.

(Continued)

*Primary Examiner* — Laura Bouchelle
(74) *Attorney, Agent, or Firm* — Mintz Levin Cohn Ferris Glovsky and Popeo, PC (57) ABSTRACT

Elements are provided for absorbing shock, pressure, impact and/or other external forces exerted upon a therapeutic fluid delivery device during use to protect the device from physical and internal damage and, thereby, according to some embodiments, maintain (for example) regulated and continuous administration of therapeutic fluid into the body.

21 Claims, 12 Drawing Sheets

(56) References Cited

FOREIGN PATENT DOCUMENTS

| WO | WO 2008/077914 | 7/2008 |
| WO | WO 2009/013736 | 1/2009 |
| WO | WO 2009/016636 | 2/2009 |
| WO | WO 2009/125398 | 10/2009 |

OTHER PUBLICATIONS

Written Opinion of the International Search Authority for PCT Application No. PCT/IL2009/000973.

* cited by examiner

SKIN SECURABLE DRUG DELIVERY DEVICE WITH A SHOCK ABSORBING PROTECTIVE SHIELD

CROSS-REFERENCE TO RELATED APPLICATIONS

The present application is a 35 U.S.C. §371 national stage entry of PCT/IL2009/000973, which has an international filing date of Oct. 11, 2009 and claims benefit and priority to U.S. provisional patent Application No. 61/104,138, filed Oct. 9, 2008, entitled "Shock Absorber for Fluid Delivery Device", the entire disclosure of which is incorporated herein by reference in its entirety.

FIELD OF THE DISCLOSURE

Embodiments of the present disclosure relate generally to systems, methods and devices for delivery of fluids. More particularly, some embodiments of the present disclosure relate to a portable fluid delivery device/system relating to a skin securable dispensing unit including one or more shock absorbers to protect the unit and its internal components and to maintain regulated fluid delivery into the patient's body.

BACKGROUND OF THE DISCLOSURE

Medical treatment of some illnesses requires sustained delivery of therapeutic fluids into various body compartments, which is carried out as subcutaneous and intra-venous injections. Such fluid delivery devices typically include reusable components such as a pumping mechanism, controller and electronics and disposable components such as a reservoir, needle assembly (e.g. cannula) and a fluid delivery tube (e.g. infusion set).

Fluid delivery devices may be carried in a pocket, attached to a belt or adhered directly to the skin. A fluid delivery device may often be subjected to undesired shock, pressure, impact and other external forces during use, which might cause harm to the physical structure and internal operation of the fluid delivery device and, in turn, negatively affect the ability of the device to administer regulated and continuous dosages of medical treatment into the body.

SUMMARY OF THE DISCLOSURE

Embodiments of the present disclosure provide systems, devices and methods for absorbing shock, pressure, impact and other external forces exerted upon a fluid delivery device, which may damage the device and/or its internal components or cause undesired occurrences such as an unintentional overdose administration of a drug to a patient. The embodiments of the present disclosure are designed to safeguard a fluid delivery device from shock, pressure, impact and other external forces that commonly occur during daily routine movements (e.g., walking, sitting, bending, or twisting) or more vigorous activities (e.g., running, jumping, kicking or participating in sports). These movements and activities include risk of hazardous physical contact or impact (e.g., getting bumped on a crowded train or getting hit with a basketball), which can harm the device as well as the therapeutic fluid (e.g., insulin) while inducing agglomerates, fibrils or reducing its potency and functionality. Preventing disruption of insulin will thus extend the duration of use of the insulin and reduce medical costs.

Implementation of the shock absorbing mechanisms for some embodiments of the present disclosure may require additional or supplemental construction to the fluid delivery device (system) or alteration or adaptation of dimensions of the fluid delivery device (system). In some embodiments, shock absorbers can also be incorporated into conventional fluid delivery devices, which employ (for example) a syringe reservoir with a propelling plunger or peristaltic pumping mechanism, without the need for any additions or dimension modifications to the fluid delivery device.

In some embodiments of the disclosure, a skin securable fluid dispensing system for regulated delivery of a therapeutic fluid into a body is provided and may include one or more (and preferably all) of the following features: a cradle configured for adhesion to a cutaneous region of the body, a therapeutic fluid delivery device including a pump and reservoir configured for attachment (which may be removable attachment) with the cradle, and at least one shock absorber positioned among the cradle and the fluid delivery device. In some embodiments, the shock absorber comprises one pad or a plurality of pads. The pads/shock absorber may comprise an elastomeric material or a spring (e.g., a wound spring, a leaf spring, and the like). The one or more pads may also be provided by either or both of the cradle and the fluid delivery device.

In some embodiments, the shock absorber is supported by an elastic member, and/or a spring (see above with regard to exemplary springs). The elastic members may be provided by one or both of the cradle and the fluid delivery device.

In some embodiments, the shock absorber may comprise one or more gaskets, where such gaskets are preferably of an elastomeric material. In some embodiments, the one or more gaskets are located along the periphery of one or both of the cradle and the therapeutic fluid delivery device.

In some embodiments, the cradle includes at least one opening such that a surface of a therapeutic fluid delivery device contacts, at least in part, the cutaneous region of the body of the user when the cradle is adhered to the cutaneous region of the body and the therapeutic fluid delivery device is attached to the cradle.

In further embodiments, the shock absorber comprises a pad provided at or adjacent an outlet port of the fluid delivery device.

In some embodiments, the shock absorber is removably coupled to one or both of the cradle and the fluid delivery device.

In some embodiments, the therapeutic fluid delivery device comprises a disposable part comprising the reservoir, and a reusable part comprising at least a portion of the pump. The reusable part may be detachably connectable to the disposable part.

In some embodiments, the therapeutic fluid delivery device further comprises one or more buttons for controlling operation of the therapeutic fluid delivery device.

In some embodiments, the skin securable fluid dispensing system further comprises a remote control for controlling operation of the therapeutic fluid delivery device.

In some embodiments, a method for maintaining regulated delivery of a therapeutic fluid into a body via a therapeutic fluid delivery device is provided, which may include one or more, and preferably many (or all) of the following steps: securing a cradle to a cutaneous region of the body, positioning at least one shock absorber between and/or among the cradle and the fluid delivery device prior to attachment of the fluid delivery device to the cradle, and attaching a therapeutic fluid delivery device to the cradle.

In some embodiments, a method for maintaining regulated delivery of a therapeutic fluid into a body via a therapeutic fluid delivery device is provided, which may include positioning at least one shock absorber on one or more of a cradle and a therapeutic fluid delivery device prior to attachment of the therapeutic fluid delivery device to the cradle.

In some embodiments, similar methods may include providing a skin securable fluid dispensing system comprising a cradle configured for adhesion to a cutaneous region of the body, a therapeutic fluid delivery device including a pump and reservoir configured for removable attachment to the cradle, and at least one shock absorber positioned among the cradle and the therapeutic fluid delivery device.

Furthermore, in some embodiments, such methods may include providing a cradle configured for adhesion to a cutaneous region of the body, and providing a therapeutic fluid delivery device including a pump and reservoir configured for removable attachment to the cradle, the cradle and/or the therapeutic fluid delivery device being provided with at least one shock absorber.

Embodiments of any of the methods may include one or more of the above described features of the device.

Advantageously, the integration of shock absorbers within or about the fluid delivery device (system) allows the user to be free from carrying supplementary auxiliary devices, such as dedicated cases, bags or external parts used to adapt the fluid delivery device for use during daily routine movements or strenuous activity, such as sports, outdoor activities or extreme weather and environmental conditions.

In the present disclosure, the term unit(s) may sometimes be used interchangeably with the term device(s), and the term device(s) may sometimes be used interchangeably with the term system(s). Such uses include, for example, a device comprising one or more (and preferably two or more) units, and a system comprising one or more (and preferably two or more) devices. Moreover, a system may also comprise one or more units.

Various objects and advantages of the present disclosure will be apparent from the following, non-limiting description of the embodiments and accompanying figures of the present disclosure, a brief description of which is provided below.

DETAILED DESCRIPTION OF THE DRAWINGS

In accordance with the foregoing objectives and others, a shock absorbing system, device and method is provided, according to at least some embodiments, to prevent damage to the physical structure and/or operation of a fluid delivery device, as well as any negative effects that such damage may have on the ability of the fluid delivery device to correctly and continuously administer medical treatment into the body.

Figure 1:
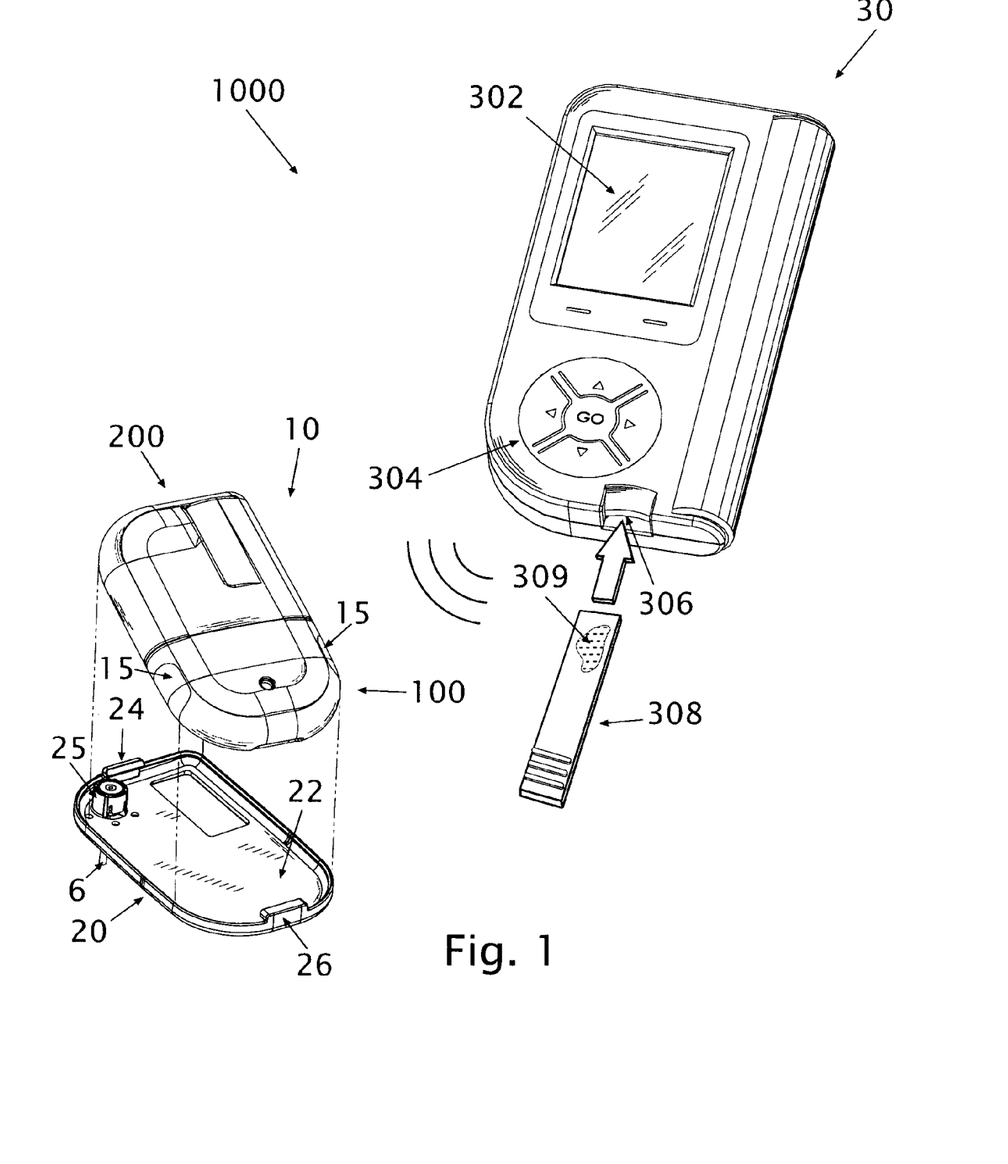
FIG. 1 is a perspective view of a fluid delivery system (e.g, a skin securable fluid dispensing device/dispensing system) comprising a dispensing unit, a cradle unit and a remote control unit according to some embodiments.

FIG. 1 illustrates a fluid delivery system 1000 (which may also be referred to as a skin securable fluid dispensing system/device) for delivering therapeutic fluid(s) (e.g., insulin) into the body of a patient. System 1000 may include a dispensing unit/device 10 (also referred to as "patch" or "dispensing patch unit" or "fluid delivery device"), a cradle unit 20 and a remote control unit 30. Fluid delivery devices are comprehensively described in co-owned U.S. Patent Publication No. 2007/0106218, filed Apr. 3, 2006, and entitled "Systems and Methods for Sustained Medical Infusion and Devices Related Thereto", and co-owned International Patent Application No. PCT/IL09/000388, filed Apr. 7, 2009, and entitled "Systems, Devices and Methods for Fluid Delivery"," the contents of which are hereby incorporated by reference in their entireties.

Furthermore, co-owned U.S. Patent Publication Nos. 2007/0191702 and 2008/0214916, the contents of which are hereby incorporated by reference in their entireties, disclose devices that include a dispensing patch unit (e.g., an insulin dispensing patch, skin securable dispensing device/system) and an analyte sensor (e.g., a continuous glucose monitor). This type of dual function device has a similar configuration to that outlined above and can also be disconnected and reconnected to and from the skin at patient's discretion.

The dispensing unit 10 can be composed of one or more parts. A two-part dispensing unit 10 embodiment may be composed of a reusable part 100 and a disposable part 200. The reusable part 100 may contain electronics, at least a portion of a driving mechanism and other components, such as detectors. The disposable part 200 may contain a reservoir and, in some embodiments, one or more batteries. In some embodiments, the disposable part 200 may be replaced after a relatively short period of time (e.g., 2-3 days, one week, or any other suitable time), whereas the reusable part 100 may be replaced after a relatively long period of time (e.g., 3 months, 6 months or any other suitable time).

The cradle unit 20 may be securable to the patient's skin (also referred to as a cutaneous region or area) via, for example, an adhesive, and it may include a cradle base 22 and a well 25 to provide for the insertion of a cannula 6 through the cradle unit 20 and into the patient's body. The well 25 may be configured as a protrusion emerging upwardly from the cradle base 22 to assist in aligning and connecting the dispensing unit 10 to the cradle unit 20. The cradle unit 20 may further include one or more anchoring mechanisms (e.g., latches 24 and 26) for securing the dispensing unit 10 to the cradle unit 20 after connection and for allowing disconnection and reconnection at the patient's discretion. A fluid delivery device employing the cradle unit 20 is described in co-owned International publication no. WO2008/078318 and co-owned U.S. Patent Publication No. 2008/0215035, both filed on Dec. 20, 2007 and entitled "Systems, Devices, and Methods for Sustained Delivery of a Therapeutic Fluid," the contents of which are incorporated herein by reference in their entireties. WO2008/078318 and US2008/0215035 claim priority to U.S Provisional Pat. App. No. 60/876,679, filed on Dec. 22, 2006, the content of which is also incorporated herein by reference in its entirety.

The remote control unit 30 may include a display/screen 302, which can be touch-sensitive and may include, without limitation, operating button(s)/switches/keypad 304. In some embodiments, the patient may also control, instruct, or command the operation of the dispensing unit 10 by one or more buttons or switches 15 disposed on the dispensing unit 10. Such buttons or switches 15 are described, for example, in co-owned International Publication No. WO2009/013736, filed on Jul. 20, 2008, the content of which is incorporated herein by reference in its entirety. WO2009/013736 claims priority to U.S. Provisional App. No. 60/961,527, the content of which is also incorporated herein by reference in its entirety. Additional operating buttons or switches may be employed on the dispensing unit 10, as well as a screen to communicate with the patient as described, for example, in co-owned International Publication No. WO2009/016636, filed on Jul. 31, 2008, the content of which is incorporated herein by reference in its entirety. WO2009/016636 claims priority to U.S. Provisional App. Ser. Nos. 60/963,148 and 61/004,019, the contents of which are incorporated herein by reference in their entireties.

The remote control unit 30 may be used for providing operating instructions to a processor of the dispensing unit 10, as well as receiving alerts and warnings from a processor. The remote control unit 30 may also be used for reading helpful information, such as ingredients values for decision making, and communicating with the dispensing unit 10 via wireless communication, including without limitation, induction, RF transmission or IR transmission, or by wired communication, including without limitation, a Universal Serial Bus ("USB") connection.

In some embodiments, the remote control unit 30 can communicate with both the dispensing unit 10 and with an external and separate blood glucose sensor/CGM (Continuous Glucose Sensor) and transfer information to the dispensing unit 10 to allow more accurate fluid delivery.

In some embodiments, the remote control unit 30 may also include an integrated blood glucose monitor, such that a blood sample 309 can be drawn from the patient and placed on a test strip 308, which can then be inserted into a dedicated slot 306 in the remote control unit 30. The data regarding the patient's blood glucose may then be transferred to a processor in the dispensing unit 10 by the remote control unit 30 for more accurate insulin delivery.

Figure 2:
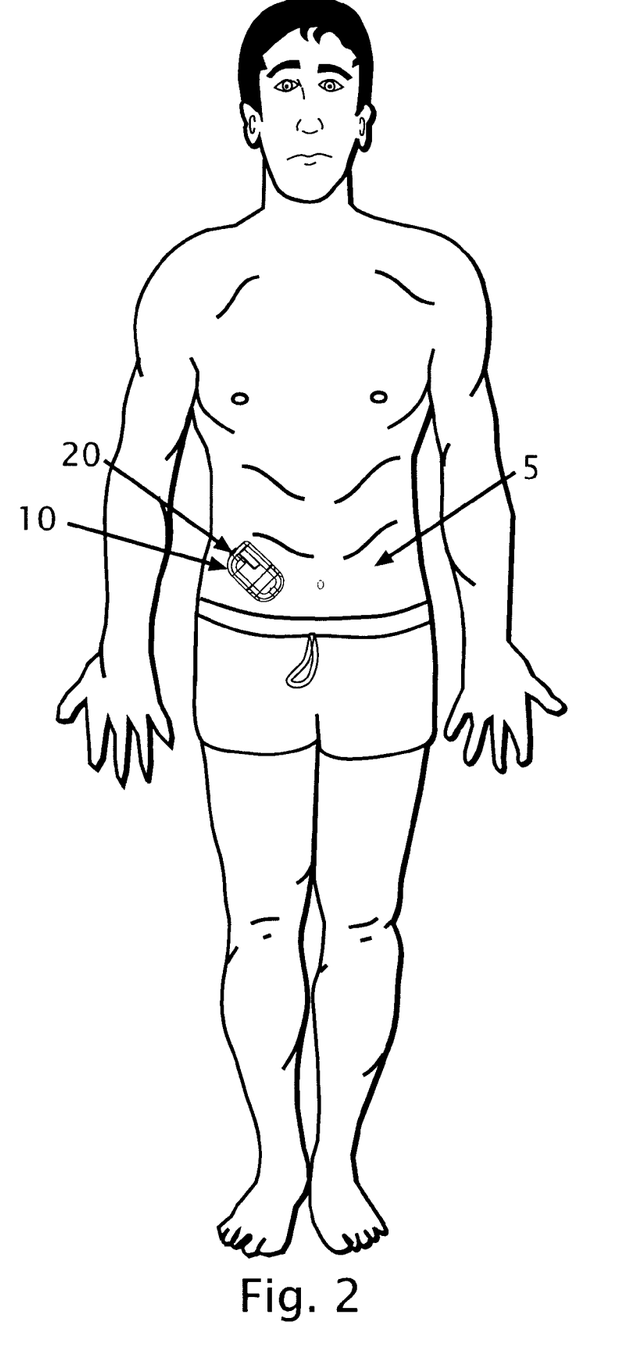
FIG. 2 illustrates a cradle unit adhered to the skin of a patient and a dispensing unit connected thereto according to some embodiments.

FIG. 2 illustrates the dispensing unit 10 secured to the patient's skin 5. The cradle unit 20 may be adhered to the patient's skin 5 and the dispensing unit 10 may then be connected/assembled to the cradle unit 20. The cradle unit 20 may be adhered to the patient's skin at the lower abdomen area, for example, or at a variety of other locations on the skin, including without limitation, shoulders, buttocks, or thighs.

Figure 3:
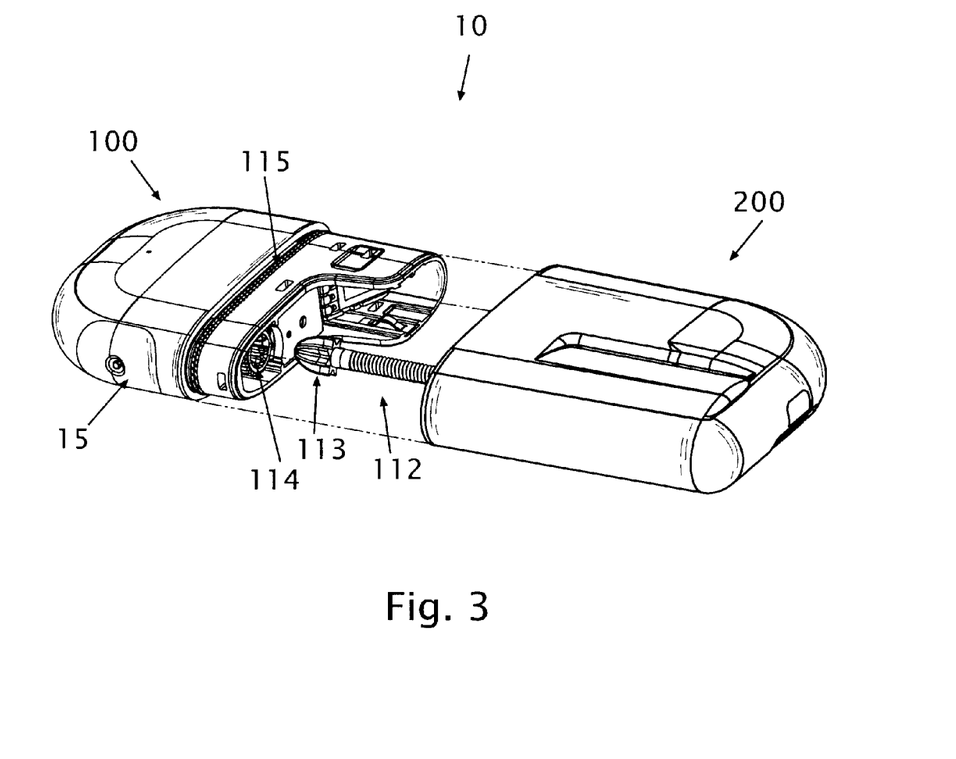
FIG. 3 is a perspective view of a two-part dispensing unit of a fluid delivery system according to some embodiments.

FIG. 3 illustrates an embodiment of a two-part dispensing unit 10 employing a syringe-piston pumping mechanism (including a syringe reservoir and a propelling piston) for dispensing fluid into the patient's body. In some embodiments, a threaded piston rod 112 is connected to a piston (not shown), which is adapted within a reservoir of the disposable part 200, and is provided with a tip 113 having teeth (also referred to as "juice extractor"). The reusable part 100 may include at least a portion of a driving mechanism having a motor and gears (not shown) which drive a threaded cylinder referred to as sleeve 114. The sleeve 114 may be configured to receive the piston rod 112 and tip 113 of the disposable part 200 upon connection of the reusable part 100 and disposable part 200, and transfer the rotational movement of the sleeve 114 to the tip 113 of the threaded piston rod 112 and to the piston itself. This rotational movement may then be translated to linear movement which displaces the piston forwardly within the reservoir and causes delivery of fluid to the patient. This embodiment is disclosed in co-owned International Patent Application No. PCT/IL09/000388, filed on Apr. 7, 2009, and entitled "Systems, devices and methods for fluid delivery", the content of which is incorporated herein by reference in its entirety.

Since the connection of the disposable part 200 and the reusable part 100, and the connection of the assembled dispensing unit 10 to the cradle unit 20, provides for direct physical contact between two or more components of the fluid delivery device, interactions between these components under certain conditions (e.g., shaking or vibrating) might cause damage to individual components or to the device as a whole. Such damage can be an acute fracture or cracks stemming from mechanical stresses or fatigue. For example, pulverization of areas which interact during connection and disconnection of the reusable part 100 and the disposable part 200 may impair the alignment of the two parts relative to each other. This pulverization can further be aggravated in the absence of a stabilizing element for preventing relative movement between the two parts. Such damages may facilitate undesired penetration of foreign substances into the dispensing unit 10, including water (e.g., during swimming or bathing) or sweat (e.g., during sport activities).

As shown in FIG. 3, in some embodiments the reusable part 100 includes a gasket 115 (e.g., O-ring), which can be made of any suitable material, including without limitation, rubber, silicone or any other resilient material capable of absorbing shocks, impacts or other external forces. When the reusable part 100 and the disposable part 200 are connected, the gasket 115 absorbs any shock or impact which might affect the area of connection between the two parts. In some embodiments, the gasket 115 can be located on the disposable part 200. The gasket 115 may be attached to the reusable part 100 or to the disposable part 200 via any technique known to one skilled in the art, including but not limited to, adhesion, close-fit under pressure, laser soldering, ultrasonic welding, over-molding or double-injection.

Figure 4:
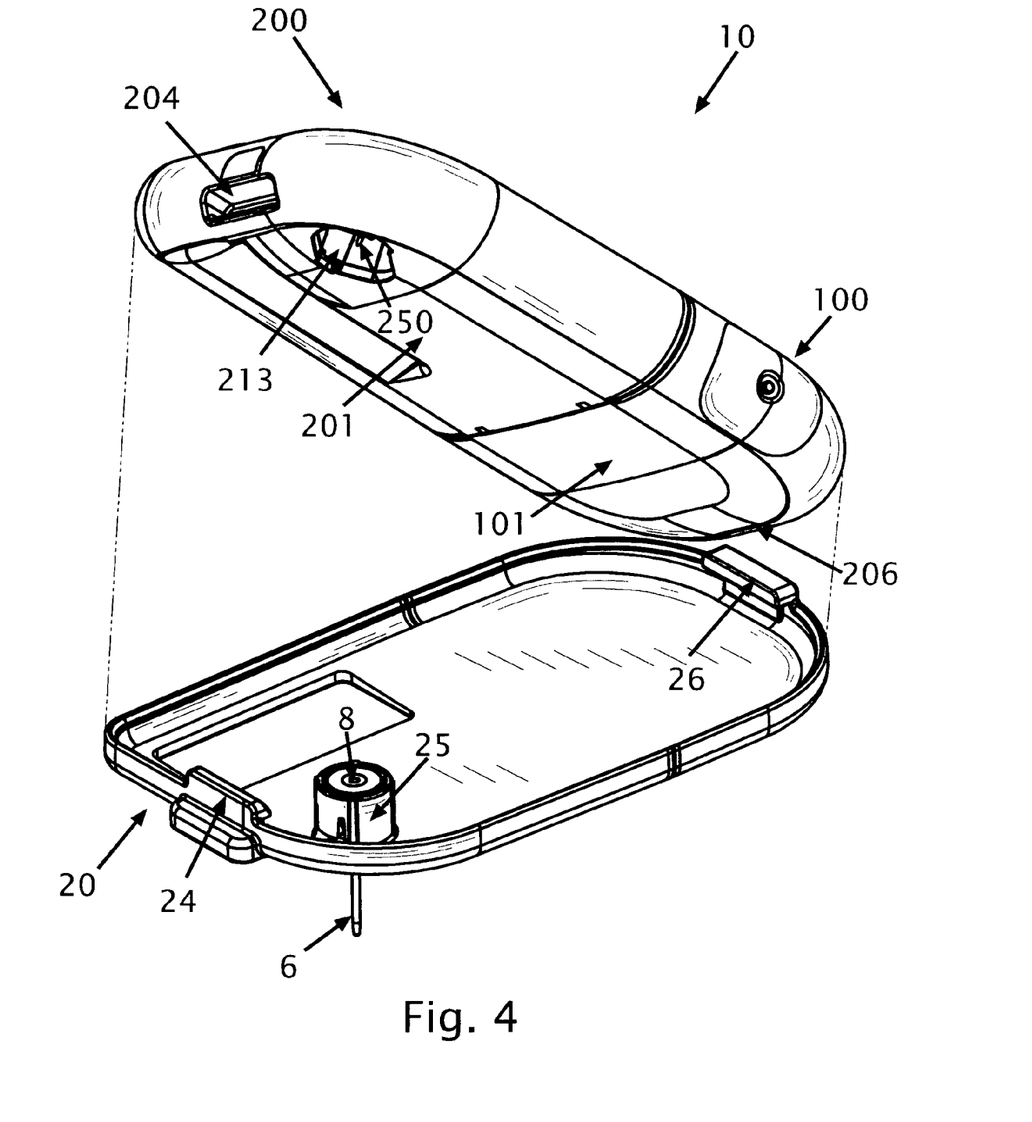
FIG. 4 is a perspective view of a two-part dispensing unit and a cradle unit of a fluid delivery system according to some embodiments.

FIG. 4 shows the connection of the dispensing unit 10 to the cradle unit 20, where the dispensing unit includes a disposable part 200 having a housing 201, and a reusable part 100 having a housing 101, connectable to the disposable part housing 201. In the figure, a cannula 6 is provided within the well 25. The dispensing unit 10 may be attached/secured to the cradle unit 20 by virtue of an arrangement of one or more grooves 204, 206, located on the dispensing unit 10 and corresponding to anchoring mechanisms (e.g., latches) 24, 26, located on the cradle unit 20. Such attachment, according to some embodiments, may be removable attachment, such that the dispensing device can be attached, removed and then reattached to the cradle. In some embodiments, the latches 24, 26 may further comprise resilient elements, including but not limited to, springs, to allow more freedom of movement when connecting or disconnecting the dispensing unit 10 to and from the cradle unit 20. In some embodiments, upon connecting the dispensing unit 10 to the cradle unit 20, the well 25 is received by an outlet port 213 of the disposable part 200. A connecting lumen 250 provided at the outlet port 213 pierces a septum 8 provided at the upper end of the cannula 6 and establishes fluid communication between the dispensing unit 10 and the cannula 6.

Figure 5A:
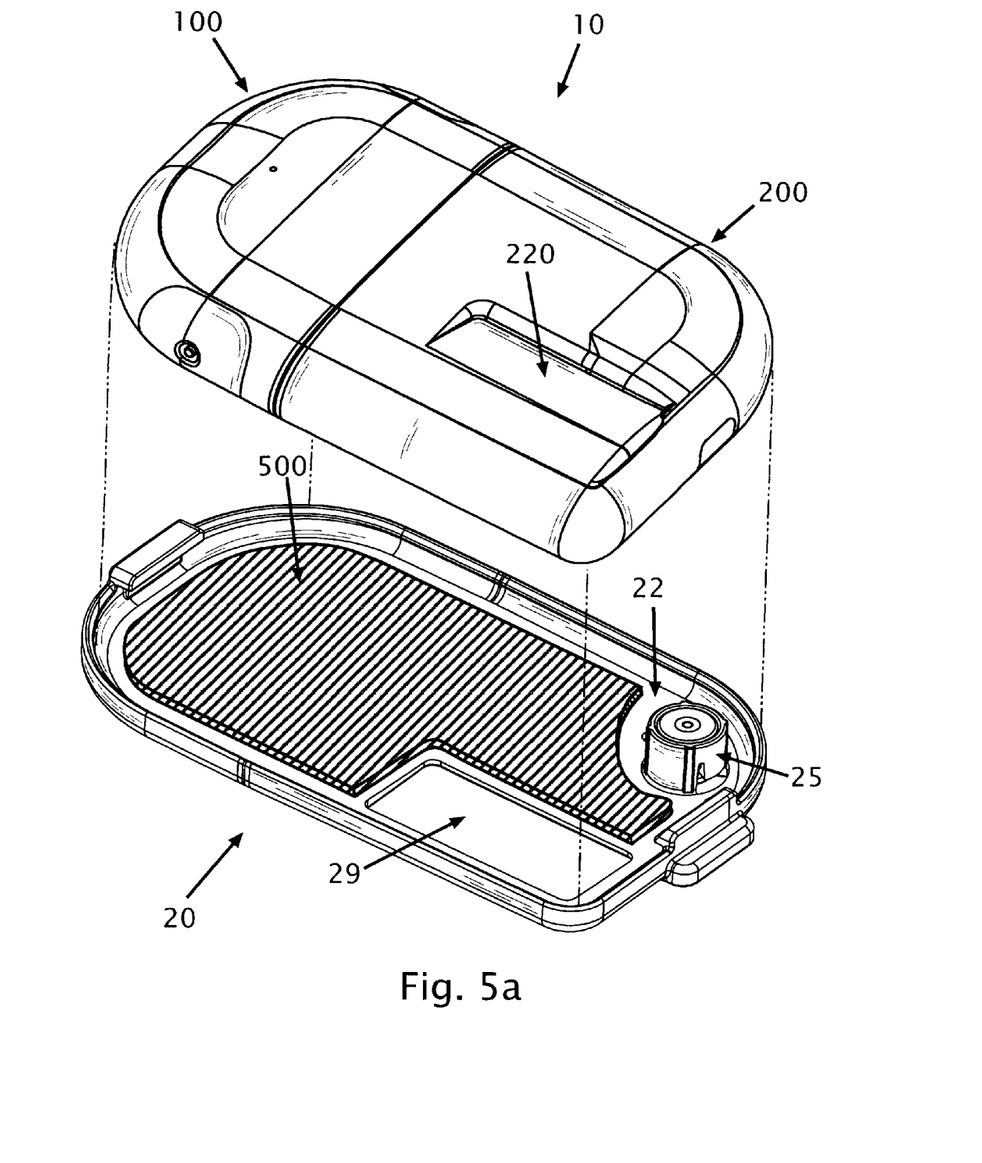
FIG. 5a is a perspective view of a fluid delivery system having a two-part dispensing unit and a cradle unit with a shock absorbing pad according to some embodiments.

FIG. 5a shows the cradle unit 20 with a shock absorbing member, for example, pad 500 ("shock absorber"), which may be formed from a variety of materials, including but not limited to, rubber, silicone, or any other soft and flexible material capable of absorbing shock, pressure, impact and other external forces. The pad 500 may be attached to the cradle base 22 by numerous means, including without limitation, adhesion, laser soldering, ultrasonic welding, mechanical fasteners or any other technique known by one of skill in the art. The pad 500 may cover the entire surface of the cradle base 22 or only a portion of the surface of the cradle base 22. In some embodiments, the pad 500 preferably provides homogenous support to the dispensing unit 10 when the unit 10 is attached/secured to the cradle unit 20. In some embodiments, the pad 500 may be attached to a bottom surface of the reusable part housing (designated by numeral 101 in FIG. 4) and/or to a bottom surface of the disposable part housing (designated by numeral 201 in FIG. 4). In some embodiments, the pad 500 is a separate component, and prior to connecting the dispensing unit 10 to the cradle unit 20 the user/patient may place the pad 500 on the cradle unit 20, or attach the pad 500 to the cradle unit and/or to a bottom surface of the dispensing unit 10 using, for example, hook-and-loop fasteners (e.g., Velcro®), magnet/s, or any other attachment technique known by one of skill in the art. The pad 500 may be reusable so that the same pad may be used with different cradles/dispensing units. The reusable pad may be detached from the cradle and/or the dispensing unit prior to replacing/disposing of the cradle and/or dispensing unit (e.g., the disposable part of the dispensing unit) and then attached to a new cradle and/or dispensing unit. In some embodiments the cradle base 22 may include an opening 29, which is preferably located beneath the reservoir 220 when the dispensing unit 10 is connected to the cradle unit 20, so that any shock, pressure, impact or other external forces applied on the reservoir area of the dispensing unit can be absorbed by the portion of the patient's skin interacting with the dispensing unit 10 through the opening 29.

Figure 5B:
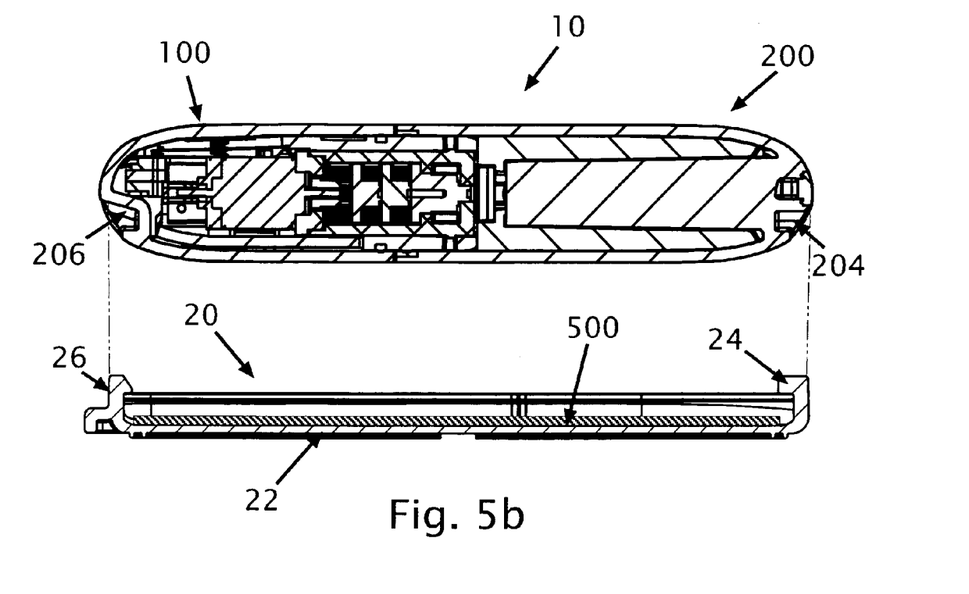
FIGS. 5b and 5c are transverse cross-sectional views of the system shown in FIG. 5a before (FIG. 5b) and after (FIG. 5c) connection of the dispensing unit to the cradle unit according to some embodiments.
Figure 5C:
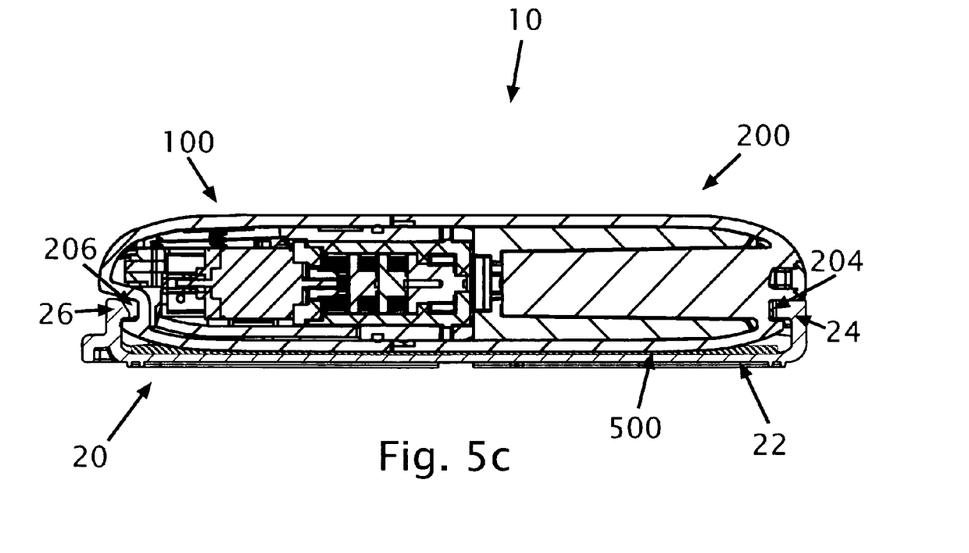

FIGS. 5b and 5c show cross-sectional views of the dispensing unit 10 before (FIG. 5b) and after (FIG. 5c) connection to the cradle unit 20. In some embodiments, the pad 500 buffers physical contact between the dispensing unit 10 and the cradle unit 20 to absorb shock, pressure, impact and other external forces exerted as a result of the interaction between the two units. In some embodiments, the thickness of pad 500 includes a low profile to avoid interference with the mechanical connection between the grooves 204, 206 and the latches 24, 26.

Figure 6A:
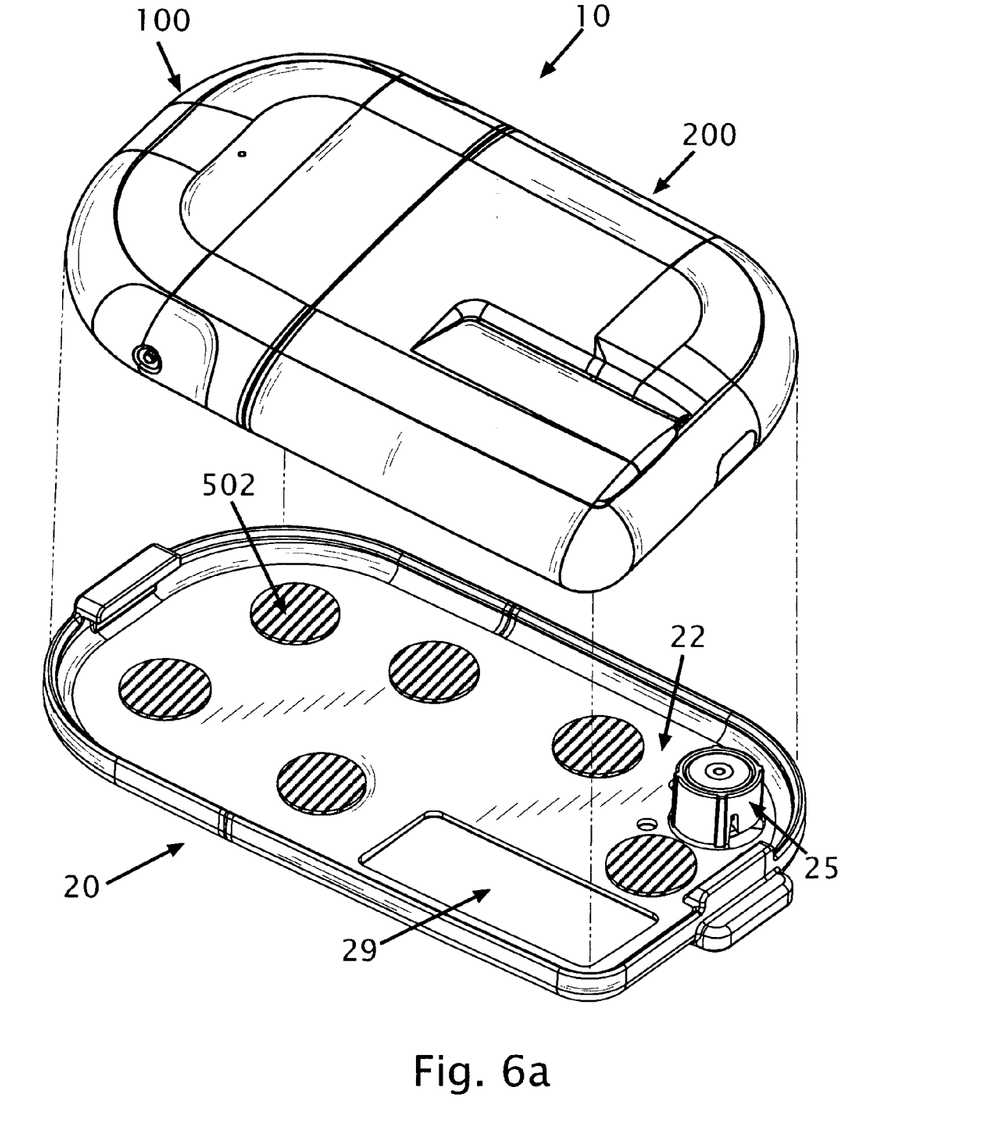
FIG. 6a is a perspective view of a fluid delivery system having a two-part dispensing unit and a cradle unit with multiple shock absorbing pads according to some embodiments.

FIG. 6a shows a cradle unit 20 provided with a plurality of circular pads 502 ("shock absorbers") disposed on the cradle base 22. The pads 502 can be formed from a variety of materials, including without limitation, rubber, silicone, or any other soft and flexible material capable of absorbing shock, pressure, impact, and other external forces. The geometric shape of the pads 502 is not limited to circles and can be formed as any shape (e.g., triangular, rectangular, pentagonal, or hexagonal) to meet particular shock absorbing needs. For example, determination of the shape of the pads 502 may be based on a force or impact distribution analysis based on the interaction between the dispensing unit 10 and the cradle unit 20. The number of pads 502 is not limited to six as shown in FIG. 6a, but, rather, may be any combination of any of shape of one or more pads. Also, the number and spatial distribution of the pads 502 according to some embodiments are designed in a variety of configurations to achieve desired and/or maximum shock absorption.

Figure 6B:
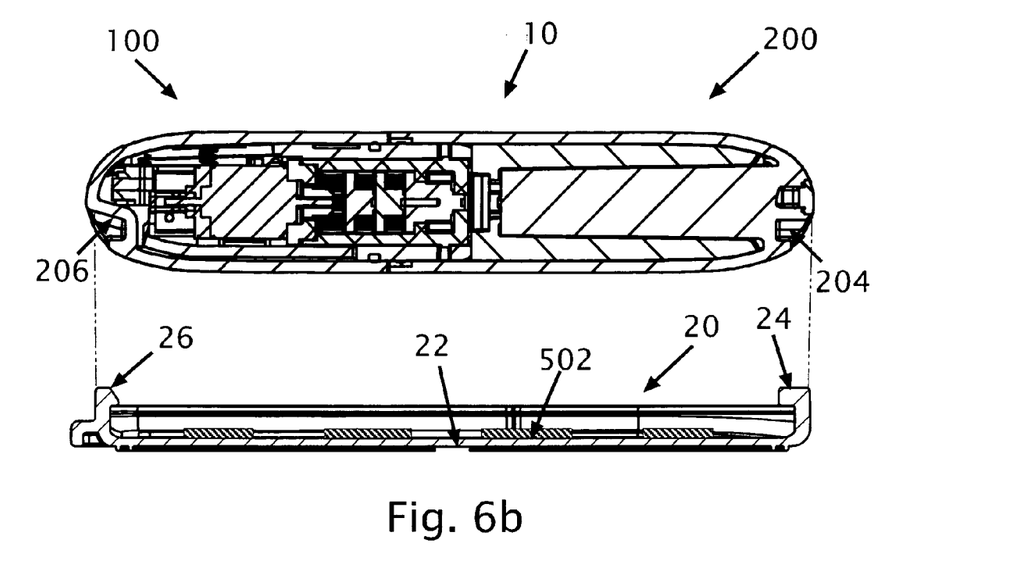
FIGS. 6b and 6c are transverse cross-sectional views of the system shown in FIG. 6a before (FIG. 6b) and after (FIG. 6c) connection of the dispensing unit to the cradle unit according to some embodiments.
Figure 6C:
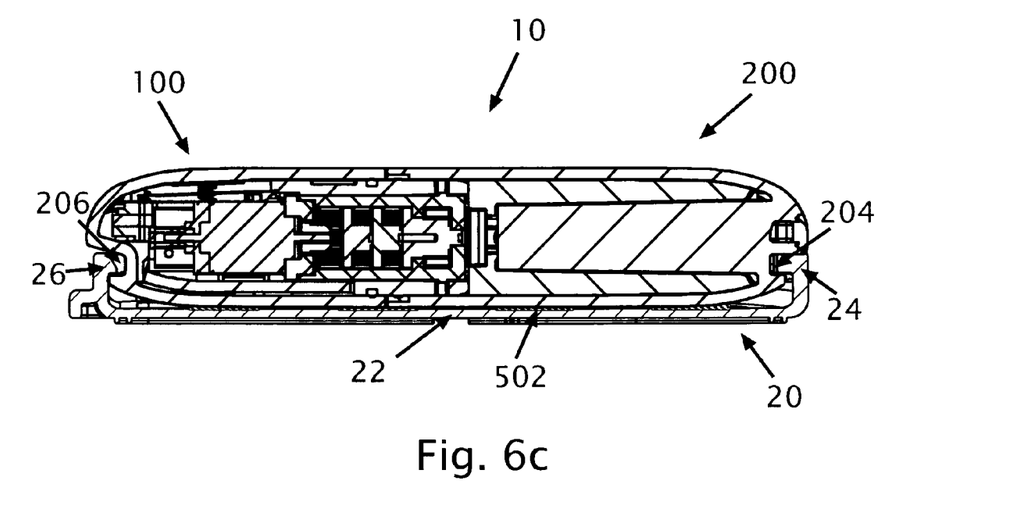

FIGS. 6b and 6c show cross-sectional views of the dispensing unit 10 before (FIG. 6b) and after (FIG. 6c) connection to the cradle unit 20. After connection of the two units, the pad(s) 502 absorb shock, pressure, impact, and other external forces from the dispensing unit 10 to the cradle 20 and/or the user's body.

Figure 7:
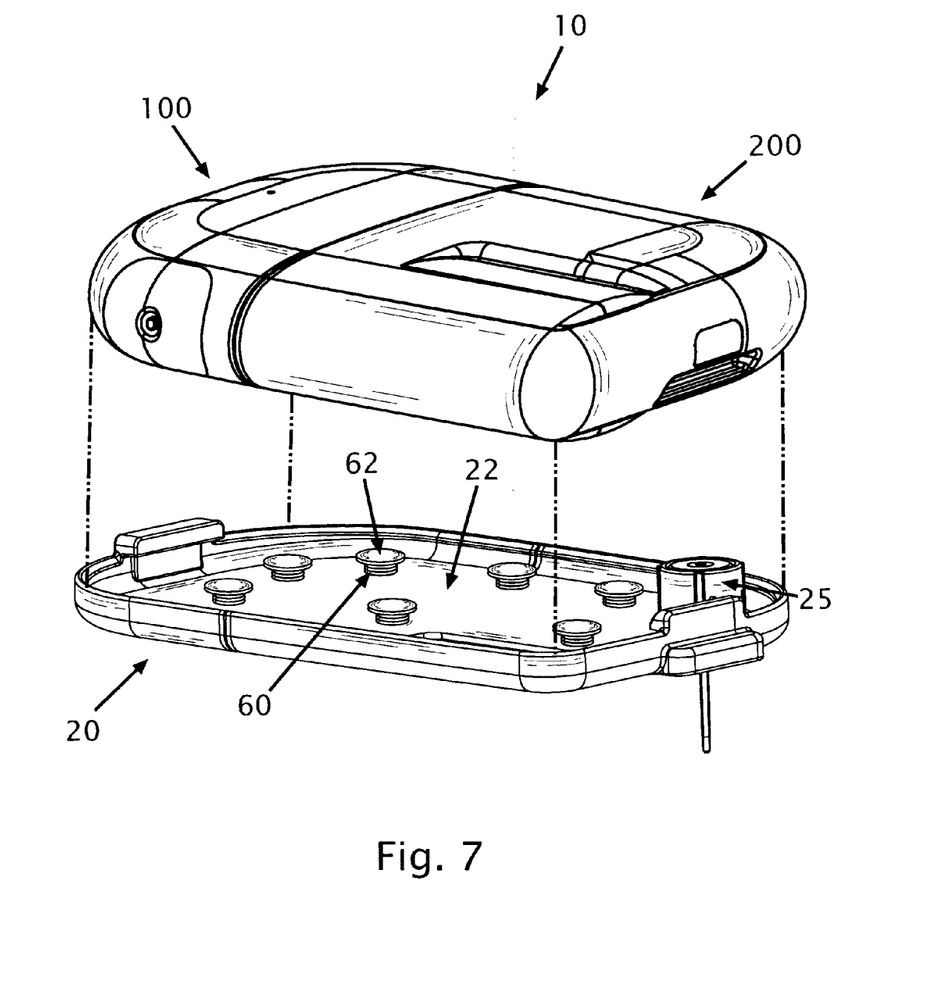
FIG. 7 is a perspective view of a fluid delivery system having a cradle unit with pads supported by springs according to some embodiments.

As shown in FIG. 7, the cradle unit 20 may be provided with one or more and, in some embodiments, a plurality of pads 62 disposed on the cradle base 22, one or more of which may be supported by corresponding elastic members 60 (e.g., springs, additional elastic material, and the like). The pads 62 are adapted to absorb shock, pressure, impact, and other external forces when the dispensing unit 10 is attached/secured to the cradle unit 20. In some embodiments, the number and spatial distribution of the elastic members 60 and pads 62 may be designed in various manners to support specific components and achieve desired and/or optimum shock absorption. For example, as shown in FIG. 7, the elastic members 60 and pads 62 may be placed on the cradle base 22 in a substantially homogeneous configuration to distribute the absorption of shock, pressure, impact, and other external forces among the elastic members 60 and pads 62 substantially equally. The elastic members' characteristics (e.g., elastic modulus) in some embodiments are configured to enable a reliable mechanical connection between the dispensing unit 10 and the cradle unit 20.

Figure 8:
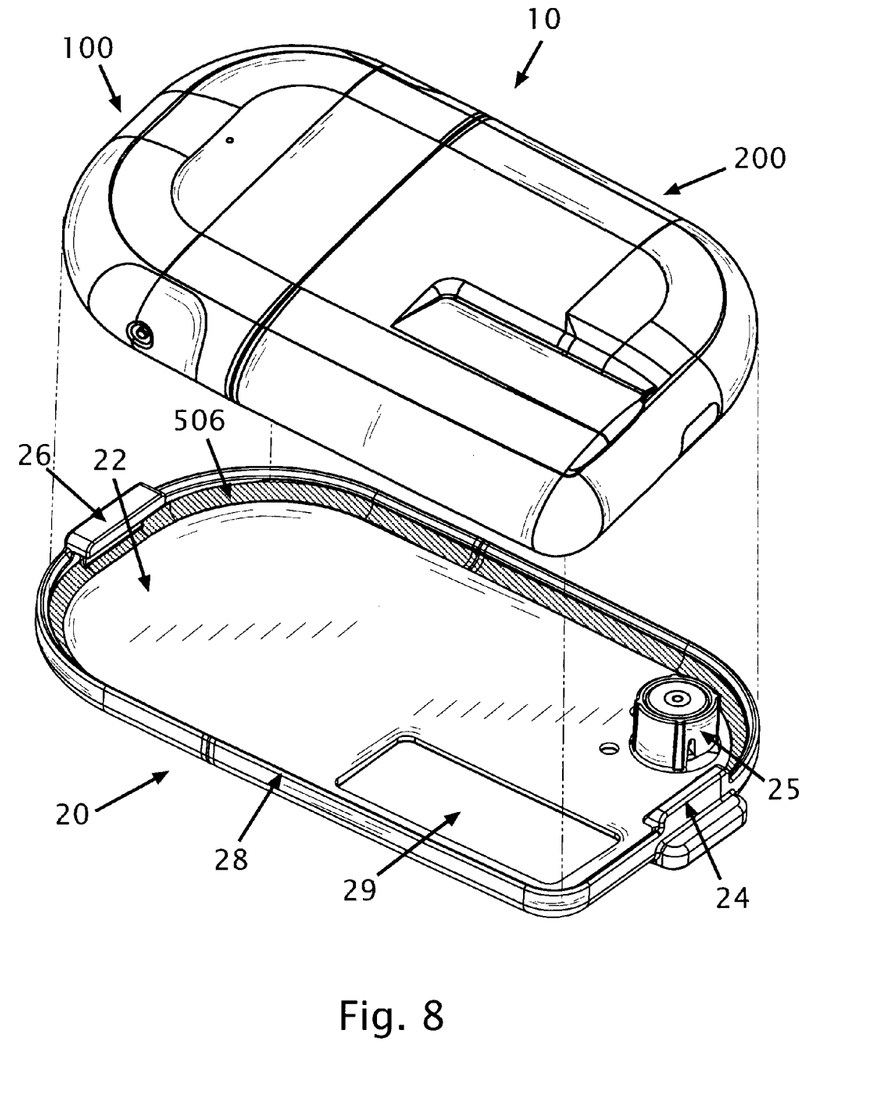
FIG. 8 is a perspective view of a fluid delivery system having a cradle unit with a peripheral gasket according to some embodiments.

FIG. 8 illustrates an embodiment in which the cradle unit 20 is provided with a gasket 506 placed along the perimeter of the cradle base 22 being supported by a cradle wall 28. The gasket 506 may be a single gasket extending along the entire periphery of the cradle base 22 or one or more gaskets extending along discrete portions of the periphery of the cradle base 22. The gasket 506 may be made from a variety of materials, including without limitation, rubber, silicone or any other flexible and resilient material capable of absorbing shock, pressure, impact, and other external forces. The gasket 506 may be further used to prevent ingression of fluids into the interface between the dispensing unit 10 and the cradle unit 20 when the two units are connected.

Figure 9:
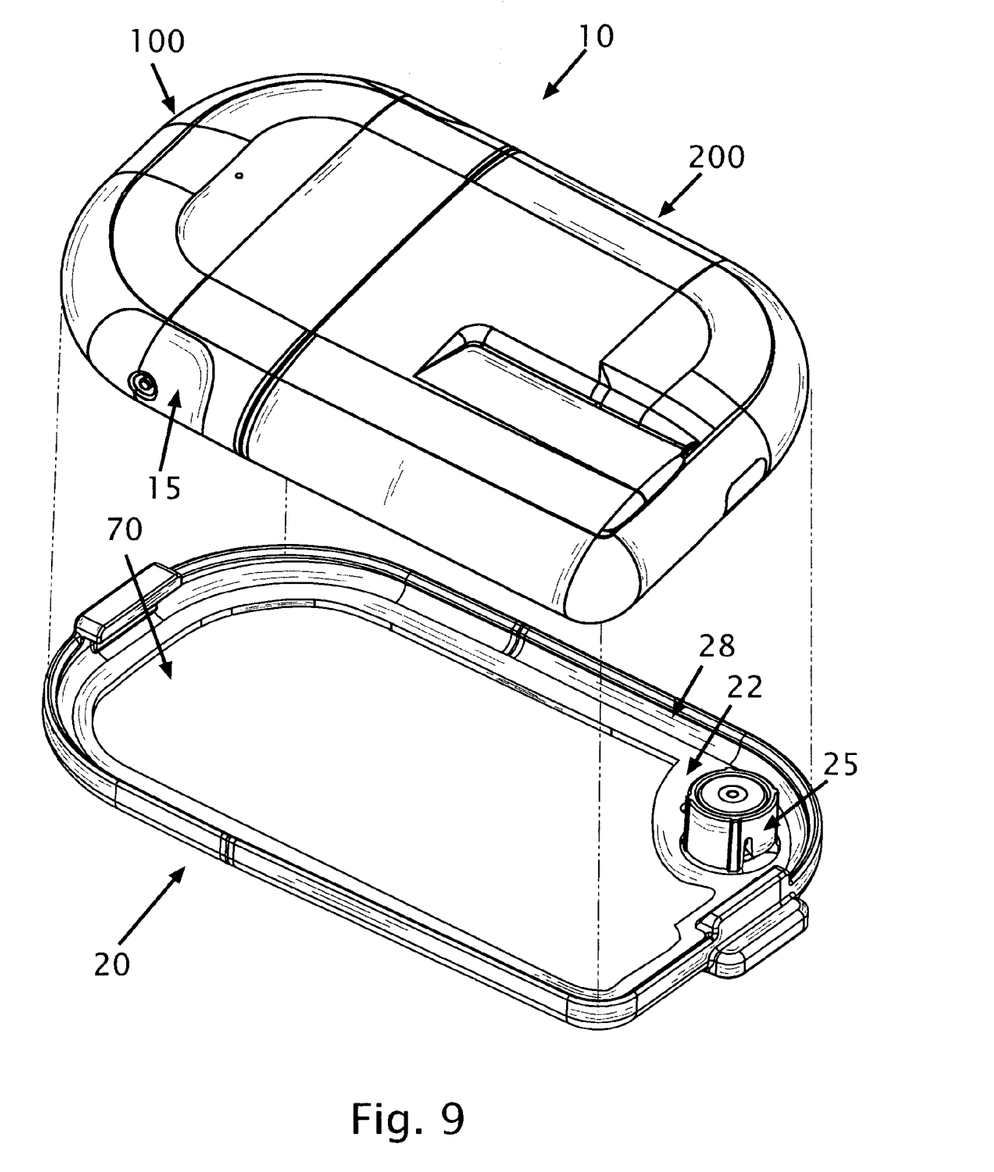
FIG. 9 is a perspective view of a fluid delivery system having a cradle unit with an opening according to some embodiments.

FIG. 9 shows a cradle unit 20 with an opening 70 created in the cradle base 22. Depending on the size of the opening 70, in some embodiments the cradle base 22 is de facto configured as a frame surrounding the opening 70. In some embodiments the cradle unit 20 may have a wall 28 along its perimeter supported by the cradle base 22. The opening 70 enables direct contact between the dispensing unit 10 and the patient's skin when the dispensing unit 10 is attached/secured to the cradle unit 20. As a result, shock, pressure, impact, and other external forces on the dispensing unit 10 can be absorbed by the portion of skin interacting with the dispensing unit 10 through the opening 70.

Figure 10:
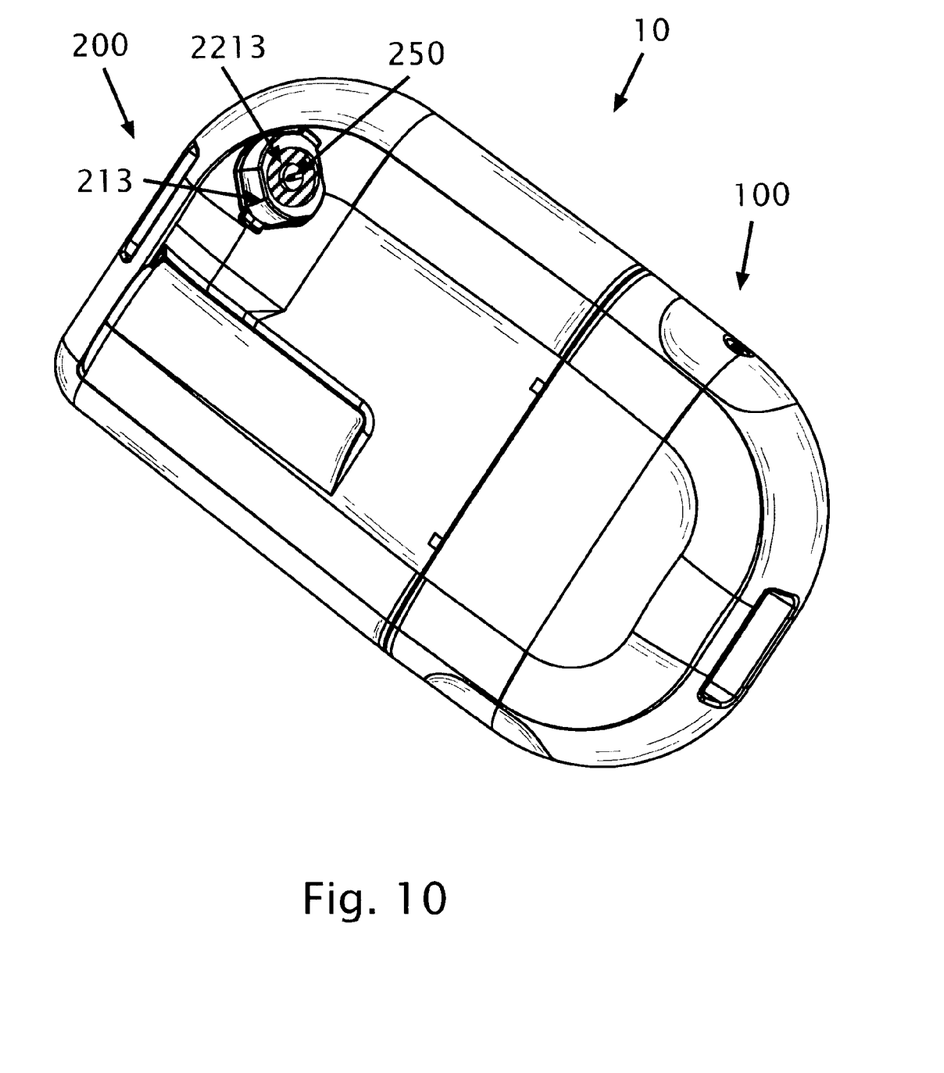
FIG. 10 is a perspective view of a dispensing unit with a shock absorbing pad located on the outlet port according to some embodiments.

FIG. 10 shows a bottom perspective view of a dispensing unit 10 having a pad 2213 encircling the connecting lumen 250 accommodated by the outlet port 213. The pad 2213 is preferably configured to absorb shock, pressure, impact and other external forces and to protect the lumen 250 and the subcutaneously-inserted cannula (not shown in FIG. 10) from mechanical damage.

Although particular embodiments have been disclosed herein in detail, they have been so described by way of example for purposes of illustration only, and are not intended to be limiting with respect to the scope of the appended claims. In particular, it is contemplated by the inventors that various substitutions, alterations, and modifications may be made without departing from the spirit and scope of the disclosure as defined by the claims. Other aspects, advantages, and modifications are considered to be within the scope of the following claims. The claims presented are representative of the inventions disclosed herein. Other, unclaimed embodiments are also contemplated. The inventors reserve the right to pursue such embodiments in later claims.

The invention claimed is:

1. A skin securable fluid dispensing system for regulated delivery of a therapeutic fluid into a body, the system comprising:
    a cradle configured for adhesion to a cutaneous region of the body;
    a therapeutic fluid delivery device including a pump and a reservoir, the therapeutic fluid delivery device being configured for removable attachment to the cradle; and
    at least one shock absorber provided on at least one of the cradle and the therapeutic fluid delivery device so as to be positioned between the cradle and the therapeutic fluid delivery device, and extending at least partly along a periphery between the cradle and the therapeutic fluid delivery device when the delivery device is attached to the cradle;
    wherein the cradle defines a first opening to allow a cannula to protrude therethrough, and at least one second opening separate from the first opening to expose therethrough at least a portion of a surface of the therapeutic fluid delivery device to the cutaneous region of the body when the cradle is adhered to the cutaneous region of the body and the therapeutic fluid delivery device is attached to the cradle.

2. The system of claim 1, wherein the at least one shock absorber comprises one or more pads provided by at least one of the cradle and the therapeutic fluid delivery device.

3. The system of claim 2, wherein the one or more pads comprise one or more of an elastomeric material and a spring.

4. The system of claim 1, wherein the at least one shock absorber comprises one or more elastic members and/or is supported by one or more elastic members provided on at least one of the cradle and the therapeutic fluid delivery device.

5. The system of claim 1, wherein the at least one shock absorber comprises one or more elastic gaskets.

6. The system of claim 1, further comprising at least one further shock absorber provided at or adjacent an outlet port of the therapeutic fluid delivery device.

7. The system of claim 1, wherein the at least one shock absorber comprises one or more of an elastomeric material and a spring.

8. The system of claim 7, wherein the elastomeric material comprises rubber and/or silicon.

9. The system of claim 1, wherein the at least one shock absorber is removably coupled to at least one of the cradle and the therapeutic fluid delivery device.

10. The system of claim 1, wherein the therapeutic fluid delivery device comprises:
    a disposable part comprising the reservoir; and
    a reusable part comprising at least a portion of the pump;
        wherein the reusable part is detachably connectable to the disposable part.

11. The system of claim 1, wherein the therapeutic fluid delivery device further comprises one or more buttons for controlling operation of the therapeutic fluid delivery device.

12. The system of claim 1, further comprising a remote control for controlling operation of the therapeutic fluid delivery device.

13. The system of claim 1, wherein the therapeutic fluid comprises insulin.

14. The system of claim 1, wherein the therapeutic fluid delivery device and the cradle include a connection means enabling disconnection and reconnection of the therapeutic fluid delivery device from and to the cradle.

15. The system of claim 14, wherein the connection means includes at least one latch located at the therapeutic fluid delivery device and at least one corresponding groove located at the cradle.

16. The system of claim 1, wherein the at least one shock absorber is configured to buffer physical contact between the therapeutic fluid delivery device and the cradle.

17. The system of claim 1, wherein the at least one shock absorber is configured to absorb external forces exerted by interaction between the therapeutic fluid delivery device and the cradle.

18. The system of claim 17, wherein the external forces include one or more of: shock, pressure and impact.

19. The system of claim 1, wherein the at least one shock absorber is configured and arranged to prevent ingression of fluids into an interface between the therapeutic fluid delivery device and the cradle when the delivery device is attached to the cradle.

20. The system of claim 1, wherein the at least one shock absorber is placed along a perimeter of the cradle and supported by a cradle wall.

21. The system of claim 1, wherein at least one of the second opening is located between the reservoir of the therapeutic fluid delivery device and the cutaneous region of the body when the cradle is adhered to the cutaneous region of the body and the delivery device is attached to the cradle.

\* \* \* \* \*